(12) United States Patent
Livnah et al.

(10) Patent No.: US 6,949,565 B2
(45) Date of Patent: Sep. 27, 2005

(54) PROTEIN KINASE INHIBITORS

(75) Inventors: Nurit Livnah, Mazkeret Batya (IL); Alexander Levitzki, Jerusalem (IL); Hadas Reuveni, Yehuda (IL)

(73) Assignees: Develogen Israel Ltd., Rehovot (IL); Yissum Research Development Co. of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 10/296,624

(22) PCT Filed: May 30, 2001

(86) PCT No.: PCT/IL01/00495

§ 371 (c)(1),
(2), (4) Date: Apr. 3, 2003

(87) PCT Pub. No.: WO01/91754

PCT Pub. Date: Dec. 6, 2001

(65) Prior Publication Data

US 2004/0019077 A1 Jan. 29, 2004

(30) Foreign Application Priority Data

May 30, 2000 (IL) .................................................. 136458

(51) Int. Cl.$^7$ ..................... A61K 31/472; C07D 217/02
(52) U.S. Cl. ........................ 514/307; 546/149; 546/148; 546/146; 546/139
(58) Field of Search .......................... 514/307; 546/149, 546/148, 146, 139

(56) References Cited

U.S. PATENT DOCUMENTS 5,245,034 A    9/1993   Hidaka et al. ............... 546/149

FOREIGN PATENT DOCUMENTS

JP    02256666    12/1989

OTHER PUBLICATIONS

Shigeo Nakamura et al.; J. Pharm. Pharmacol. 1993, 45:268–273; Effects of Isoquinolinesulphonamide Compounds on Multidrug–resistant P388 Cells.

Shinya Wakusawa et al.; Molecular Pharmacology, 41:1034–1038; Overcoming of Vinblastine Resistance by Isoquinolinesulfonamide Compounds in Adriamycin–Resistant Leukemia Cells.

K.–I. Miyamoto et al.; Cancer Letters, 51:37–42; Circumvention of multidrug resistance in P388 murine leukemia cells by a novel inhibitor of cyclic AMP–dependent protein kinase, H–87.

V. John et al.; Pharm Pharmacol Lett (1994), 3:190–193; The effect of cyclic AMP–dependent protein kinase inhibitors on electrical resistance in the cell culture model for the blood–brain barrier.

*Primary Examiner*—Charanjit S. Aulakh
(74) *Attorney, Agent, or Firm*—Winston & Strawn LLP

(57) ABSTRACT

Novel isoquinoline derivatives which are useful as inhibitors of protein kinases for experimental, medical, and drug design purposes are disclosed. Preferred compounds which are specific inhibitors of protein kinase B are also disclosed. Furthermore, pharmaceutical compositions comprising these protein kinase inhibitors, and methods of using such compositions for treatment and diagnosis of cancers, diabetes, cardiovascular pathologies, hemorrhagic shock, obesity, inflammatory diseases, diseases of the central nervous system, and autoimmune diseases, are also disclosed.

21 Claims, 6 Drawing Sheets

Figure 2
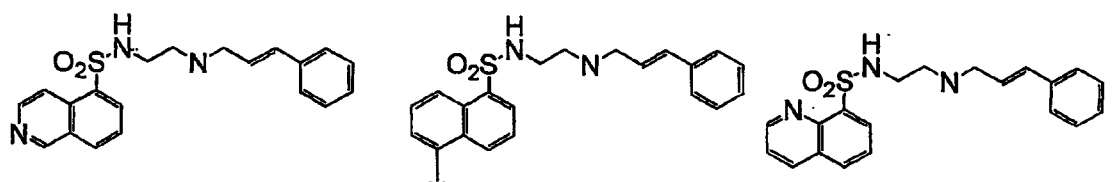
IC50=10μM    IC50>200μM    IC50>200μM
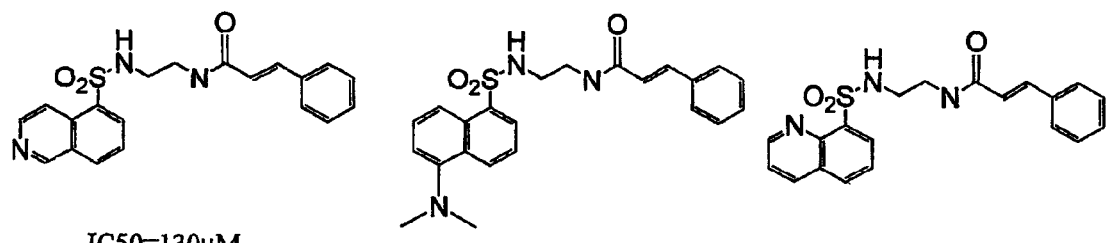
IC50=130μM    IC50>200μM    IC50>200μM
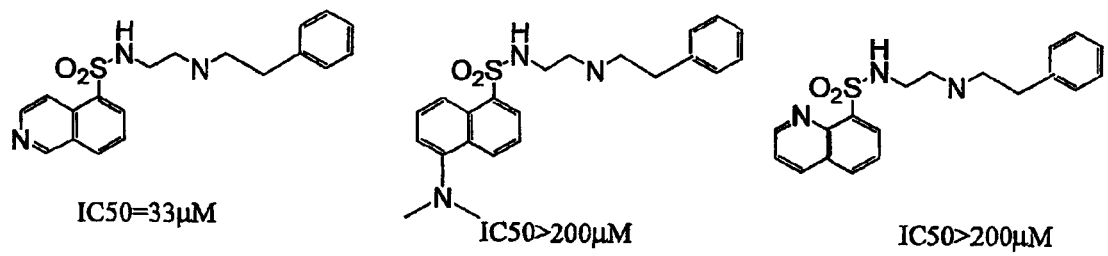
IC50=33μM    IC50>200μM    IC50>200μM Figure 3
| Structure | Inhibitor | IC$_{50}$ µM PKB | PKA |
|---|---|---|---|
| 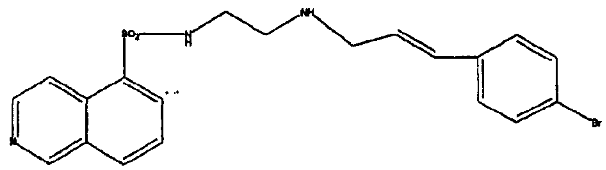 | H-89 | 2 | 0.035 |
| 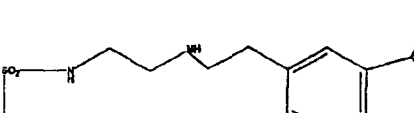 | 4-A2 | 6.5 | 0.16 |
| 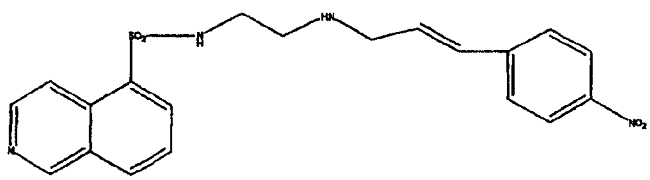 | 4-A5 | 2.6 | 0.14 |
| 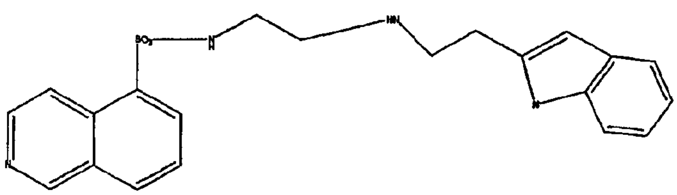 | 4-A10 | >100 | 12 |
| 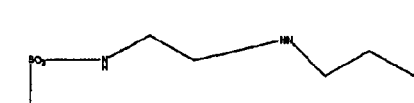 | 4-A12 | 28 | 0.52 |

Figure 4

| Structure | PKB μM | PKA μM |
|---|---|---|
| Isoquinoline-5-sulfonamide-NH-CH₂-NH-CH₂CH₂-C₆H₄-Br | 2.9 | 0.048 |
| Isoquinoline-5-sulfonamide-NH-CH₂-NH-CH₂-CH(Ph)₂ | 3.7 | 9 |
| Isoquinoline-5-sulfonamide-NH-CH₂-NH-CH₂CH₂CH₂-CH(4-F-C₆H₄)₂ | 5.6 | 8.5 |
| Isoquinoline-5-sulfonamide-NH-CH₂-NH-CH₂-C(CH₃)=C(Cl)-(4-biphenyl-F) | 13 | 2.8 |

| Structure | Inhibition | |
|---|---|---|
| Isoquinoline-5-sulfonamide-NH-CH₂-NH-CH₂CH₂-C(Ph)(CN)(Ph) | 81% | 65% |
| Isoquinoline-5-sulfonamide-NH-CH₂-NH-CH₂CH₂-C(=O)-Ph | 75% | 44% |

PROTEIN KINASE INHIBITORS

FIELD OF THE INVENTION

The present invention relates to isoquinoline derivatives, to pharmaceutical compositions containing the isoquinoline derivatives, their use as inhibitors of protein kinase, as well as to processes for the preparation and use of such molecules.

BACKGROUND OF THE INVENTION

Protein kinases are involved in the signal transduction pathways linking growth factors, hormones and other cell regulation molecules to cell growth, survival and metabolism under both normal and pathological conditions. The superfamily of protein kinases includes protein kinase A and protein kinase C, as well as the more recently discovered protein kinase B (PKB). PKB is a direct downstream effector of phosphatidylinositol 3-kinase (PI 3-kinase) and is activated in response to insulin or growth factors (for review see Kandel and Hay, Exp. Cell Research 253, 210, 1999).

PKB activation involves phosphorylation of two amino acid residues, Ser473 and Thr308. PKB is a newly recognized anti-apoptotic protein kinase whose activity is strongly elevated in human malignancies. PKB was originally discovered as a viral oncogene v-Akt in rat T-cell leukemia It was later established that v-Akt is the oncogenic version of a cellular enzyme PKB/c-Akt, in which a truncated viral group specific antigen, gag, is fused in frame to the full length Akt-1 and is membrane bound whereas PKB/c-Akt is cytoplasmic. Sequencing of Akt revealed a high degree of homology to PKA (~75%) and PKC isozymes (~50%), a fact which lent to its rechristening as PKB.

The enzyme is activated by the second messenger PIP3 produced by PI'-3-kinase. PIP3 binds to the pleckstrin homology (PH) domains of PKB, recruits it to the membrane where it is phosphorylated and converted to its activated form. Since PKB activation is PI'-3-kinase dependent, the persistent activation of certain protein tyrosine kinases, such as IGF-1 receptor, EGF receptor, PDGF receptor, pp60c-Src, and the like, leads to the persistent activation of PKB which is indeed encountered in many tumors. Deletions in the gene coding for the tumor suppressor PTEN also induce the persistent activation of PKB/cAkt since it is the negative regulator of this enzyme. Also, PKB is overexpressed in 15% of ovarian cancers, 12% of pancreatic cancers and 3% of breast cancers, and was shown to produce a survival signal that protects cells from apoptosis thus contributing to resistance to chemotherapy.

These molecular properties of PKB and its central role in tumorigenesis, implies that this protein kinase may be an attractive target for novel anti-cancer agents. To date no specific inhibitors of PKB are known in the art, nor are any of the disclosed inhibitors of protein kinases A and C known to act on PKB.

Hidaka H. et al. (Biochemistry, 32, 5036, 1984) describe a class of isoquinolinesulfonamides having inhibitory activity towards cyclic nucleotide dependent protein kinases (PKA and PKG) and protein kinases C (PKC). The same class of compounds is claimed in EP 061673, which discloses said compounds as having cardiovascular activity. Additional derivatives of isoquinolinesulfonyl were disclosed by Hidaka in EP 109023, U.S. Pat. Nos. 4,456,757, 4,525,589, and 4,560,755.

Antitumor activity has been suggested for some of these isoquinolinesulfonamides. Martell R. E. et al. (Biochem. Pharm., 37, 635, 1988) found effects of two isoquinolinesulfonamides, namely 1-(5-isoquinolinsulfonyl)-2-methylpiperazine (H-7) and N-[2-guanidinoethyl]-5-isoquinolinesulfonamide (HA-1004), which have a certain selectivity for PKC and cyclic nucleotide dependent protein kinases, respectively, on calcitriol-induced cell differentiation. Further, Nishikawa M. et al., Life Sci., 39, 1101, 1986), demonstrate that the same compound H-7 inhibits cell differentiation induced by phorbol diester.

International PCT application WO 93/13072 discloses 5-isoquinolinesulfonamide derivatives as protein kinase inhibiting agents wherein the claimed compounds all contain two sulfonyl moieties.

Other classes of compounds known in the prior art (EP-A-397060, DE-A-3914764 and EP-A-384349) showed the capacity of inhibiting protein kinases, however, said compounds have a chemical structure which is totally different from that of the compounds of the present invention. In addition, international PCT application WO 98/53050 discloses short peptides derived from the HJ loop of a serine/threonine kinase which modulate the activity of serine/threonine kinases.

The minimal consensus sequence for efficient phosphorylation by PKB was found by Alessi et al. (Fed. Eur. Biochem. Soc., 399, 333, 1996). This is a 7-mer motif with the most active peptide substrate having the sequence Arg-Pro-Arg-Thr-Ser-Ser-Phe (SEQ ID NO. 1). International application WO 97/22360 discloses certain PKB substrate peptides having 7-amino acids length, useful as substrate for measuring PKB activity.

Obata et al. (J. Biol. Chem., 17, 36108, 2000) described the use of an oriented peptide library approach to determine optimal amino acid sequence of the PKB substrate. All the substrates identified contained the known motif having the sequence Arg-Xaa-Arg-Xaa-Saa-Ser/Thr (SEQ ID NO. 2).

SUMMARY OF THE INVENTION

It is an object of the present invention to provide small molecules useful as inhibitors of protein kinases for medical, therapeutic and drug design purposes. It is yet another object of the present invention to provide such molecules which are selective inhibitors of protein kinase B.

One aspect of the present invention involves the preparation of novel compounds which inhibit the activity of protein kinases. It has now surprisingly been found that certain novel derivatives of isoquinolinesulfonamides, are protein kinase inhibiting agents, which proved to be selectively active towards a specific type of protein kinase, namely protein kinase B.

Another aspect of the present invention is directed to pharmaceutical compositions comprising as an active ingredient at least one novel isoquinoline inhibitor of protein kinase and to methods for the preparation of pharmaceutical compositions comprising such inhibitors of protein kinases.

Another aspect of the present invention is directed to the use of pharmaceutical compositions comprising these protein kinase inhibitors for production of medicaments useful for the treatment or diagnosis of diseases and disorders. The present invention discloses methods of treatment of disorders wherein protein kinase is involved including but not limited to cancers, cardiovascular pathologies, hemorrhagic shock, obesity, inflammatory diseases, diseases of the central nervous system, and autoimmune diseases.

It is another object of the present invention to provide methods for modulating the activity of protein kinases in a subject, comprising administering a therapeutically effective amount of protein kinase inhibitors.

Further objects of the present invention are directed to methods for the diagnosis of diseases including in-vitro diagnosis using the compounds of the present invention, and in-vivo diagnosis involving administering a pharmaceutical composition comprising a diagnostically useful amount of a protein kinase inhibitor prepared according to the principles of the present invention.

It is yet another object of the present invention to provide small molecules that mimic the ATP molecule that binds to the PKB which are further conjugated to a peptide substrate or peptido-mimetic substrate of PKB. Such chimeric compounds according to the invention preferably serve as PKB inhibitors with improved activity and selectivity.

A preferred embodiment according to the present invention has the general formula I:

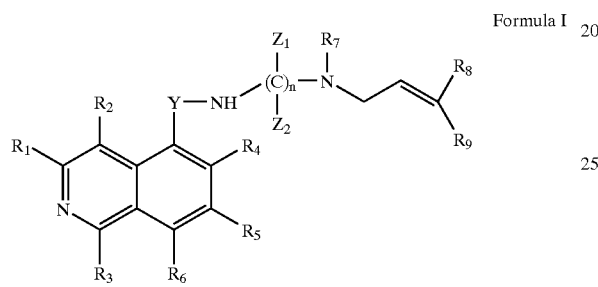

Formula I wherein:

$R_1$–$R_6$ are each independently selected from the group consisting of hydrogen, a lower alkyl group, a lower alkoxy group, a phenyl group, a lower alkyl substituted with at least one substituent selected from the group consisting of a phenyl group, a halogen, hydroxyl, thiol, nitro, cyano, or amino group;

Y is selected from the group consisting of sulfonyl, carbonyl, carbamate or carbamoyl;

$R_7$ is selected from the group consisting of hydrogen, a lower alkyl group, a lower alkoxy group, a phenyl group, a lower alkyl substituted with at least one substituent selected from the group consisting of a phenyl group, a halogen, hydroxyl, thiol, nitro, cyano, or amino group;

n is 1–2;

$Z_1$ and $Z_2$ are each independently hydrogen or a lower alkyl group;

$R_8$ and $R_9$ are each independently selected from the group consisting of a substituted or unsubstituted phenyl, alkylaryl, naphthyl, quinolyl or a halogen, with the proviso that at least one of $R_8$ and $R_9$ is aromatic.

One currently more preferred embodiment according to the present invention is the compound of Formula II:

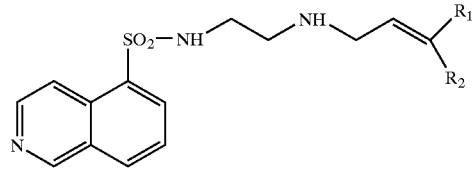

Formula II wherein $R_1$ and $R_2$ are independently selected from the group consisting of substituted or unsubstituted phenyl, alkylaryl, naphthyl, quinolyl, or a halogen, with the proviso that at least one of $R_1$ and $R_2$ is aromatic.

Another currently more preferred embodiment of the present invention comprises a compound of Formula III:

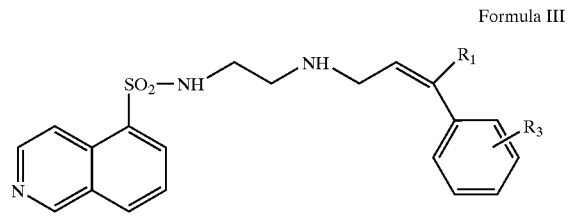

Formula III wherein $R_1$ is selected from the group consisting of substituted or unsubstituted phenyl, alkylaryl, naphthyl, quinolyl, or a halogen; and $R_3$ is selected from the group consisting of hydrogen, a lower alkyl group, a lower alkoxy group, substituted or unsubstituted phenyl group, a lower alkyl substituted with at least one substituent selected from the group consisting of a phenyl group, a halogen, hydroxyl, thiol, nitro, cyano, or amino group.

One currently most preferred embodiment of the present invention is the compound N1-(8-sulfonamide-5-isoquinoline)-N2-(3,3-diphenyl-2-propenyl)-ethylenediamine, denoted hereinbelow as B-11-I of Formula IV:

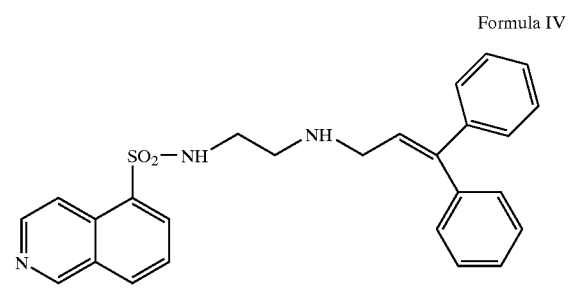

Formula IV

An additional most preferred embodiment of the present invention comprises a compound of Formula V:

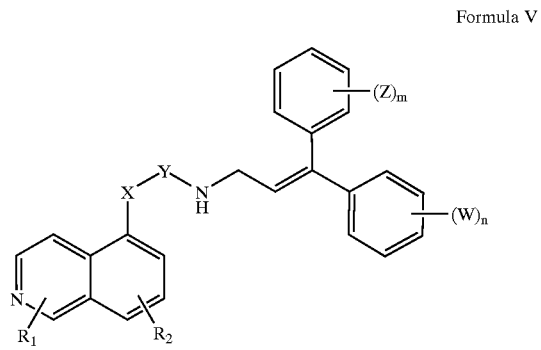

Formula V wherein:

X is selected from the group consisting of $SO_2$—NH, S and O;

Y represents substituted or unsubstituted alkylene of 1–4 carbons atoms;

$R_1$ and $R_2$ are independently selected from the group consisting of hydrogen, a lower alkyl group, a lower alkoxy group, substituted or unsubstituted phenyl group, a lower alkyl substituted with at least one substituent selected from the group consisting of a phenyl group, a halogen, hydroxyl, thiol, nitro, cyano, or amino group;

Z and W at each occurrence are independently selected from the group consisting of hydrogen, a halogen, $CF_3$, a lower alkoxy, OPhe, alkyl, substituted alkyl, phenyl or substituted phenyl;

m and n are each independently 0–4;

or, Z and W are connected via a bridge comprising 0–4 carbon atoms connected covalently through single or double bonds.

It is understood that if m or n is greater than 1 each substituent may be the same or different.

An example of a currently more preferred compound according to formula V is a compound of formula VI:

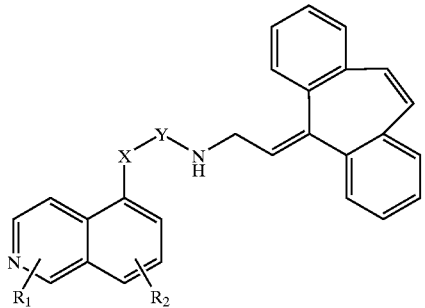

Formula VI wherein:

X is selected from the group consisting of $SO_2$—NH, S and O;

Y represents substituted or unsubstituted alkylene of 1–4 carbons atoms;

$R_1$ and $R_2$ are independently selected from the group consisting of hydrogen, a lower alkyl group, a lower alkoxy group, substituted or unsubstituted phenyl group, a lower alkyl substituted with at least one substituent selected from the group consisting of a phenyl group, a halogen, hydroxyl, thiol, nitro, cyano, or amino group.

Essentially all of the uses known or envisioned in the prior art for protein kinase inhibitors, can be accomplished with the molecules of the present invention. These uses include therapy and diagnostic techniques.

By way of exemplification, the compounds disclosed in the present invention were selected for inhibition of Protein kinase B. Using the preparations and methods disclosed herein it is possible to obtain compounds which inhibit the activity of other types of protein kinases.

BRIEF DESCRIPTION OF THE DRAWINGS

FIG. 2. Miniseries of H-89 analogs optimizing the chemistry of the bond connecting regions B and C. An amine and an amide bond were synthesized and compared, for three different bicyclic A cores and three different C regions FIG. 3. Structure Activity Relation (SAR) of purified compounds with modified C section.

FIG. 4. SAR of the effect of an additional substitution near the aromatic residue of region C.

DETAILED DESCRIPTION OF THE INVENTION

Figure 1:
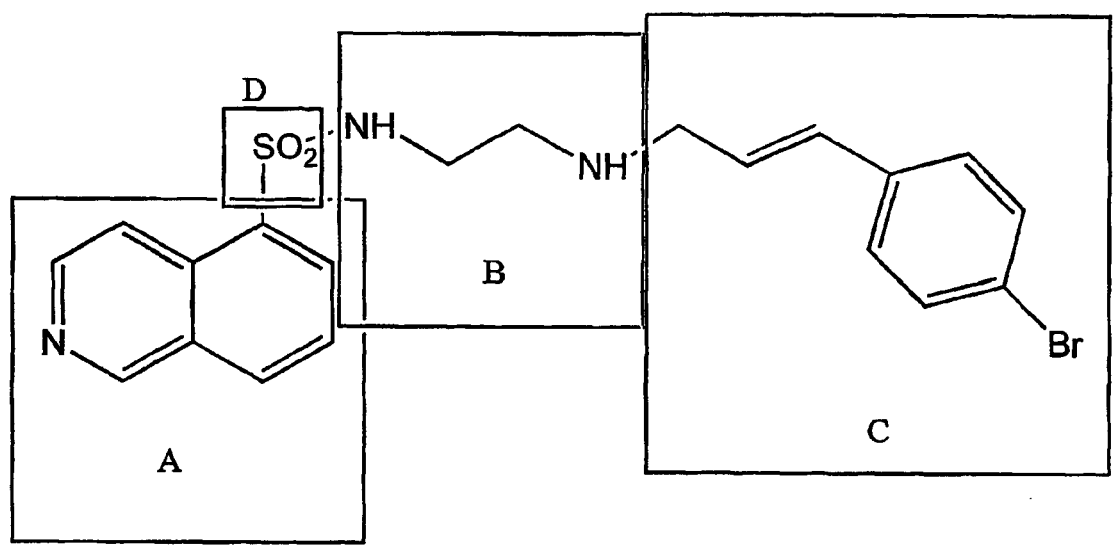
FIG. 1. The known molecule H-89 and the various diversity regions in its structure. A is the core, B is the bridge, C is the tail and D is the moiety connecting A and B.

It is now disclosed that small molecules according to the present invention are inhibitors of protein kinases. In general, it has now been discovered that the active molecules according to the present invention share certain structural motifs, which may be construed as an "ATP mimetic" motif. This motif, in the broadest terms may be defined as comprising four distinct regions, which are defined by their functional and chemical attributes, as will be exemplified hereinbelow.

The disclosed protein kinase inhibitors are small molecules which exhibit enhanced specificity toward certain protein kinase subtypes. In principle, the present invention provides for the first time selective inhibitors of protein kinase B. The preferred molecules generally have a molecular weight of less than about 1000 daltons. These and further advantages over the background art will become apparent from the description of the currently preferred embodiments of the present invention.

The utility of the compositions according to the invention can be established by means of various assays as are well known in the art. The preferred compounds of the present invention were found to be active in a panel of in-vitro assays, in inhibiting the activity of protein kinases and in induction of apoptosis in cancer cells.

Pharmaceutical compositions according to the present invention comprising pharmacologically active protein kinase inhibitors and a pharmaceutically acceptable carrier or diluent represent another embodiment of the invention, as do the methods for the treatment of a mammal in need thereof with a pharmaceutical composition comprising an effective amount of a protein kinase inhibitor according to the invention. Methods of treatment using the compositions of the invention are useful for therapy of cancers, diabetes, cardiovascular pathologies, hemorrhagic shock, obesity, inflammatory diseases, diseases of the central nervous system, and autoimmune diseases using such compositions. The pharmaceutical compositions according to the present invention advantageously comprise at least one protein kinase inhibitor. These pharmaceutical compositions may be administered by any suitable route of administration, including topically or systemically. Preferred modes of administration include but are not limited to parenteral routes such as intravenous and intramuscular injections, as well as via nasal or oral ingestion.

In the specification and in the claims the term "therapeutically effective amount" refers to the amount of protein kinase inhibitor or composition comprising same to administer to a host to achieve the desired results for the indications described herein, such as but not limited of cancers, diabetes, cardiovascular pathologies, hemorrhagic shock, obesity, inflammatory diseases, diseases of the central nervous system, and autoimmune diseases.

In the specification and in the claims the term "protein kinase" refers to a member of an enzyme superfamily which functions to phosphorylate one or more protein as described above.

As used herein and in the claims, the term "inhibitor" is interchangeably used to denote "antagonist" these terms define compositions which have the capability of decreasing certain enzyme activity or competing with the activity or function of a substrate of said enzyme.

Certain abbreviations are used herein to describe this invention and the manner of making and using it. For instance, ATP refers to adenosine three phosphate, BSA refers to bovine serum albumin, BTC refers to bis-(trichloromethyl)carbonate or triphosgene, DCM refers to dichloromethane, DIEA refers to diisopropyl-ethyl amine, DMF refers to dimethyl formamide, EDT refers to ethanedithiol, EDTA refers to ethylene diamine tetra acetate, ELISA refers to enzyme linked immuno sorbent assay, EGF refers to epithelial growth factor, FACS refers to fluorescence assisted cell sorter, HA refers to hemagglutinin, HBTU refers to 1-hydroxybenztriazolyltetramethyl-uronium, HEPES refers to 4-(2-hydroxyethyl)-1-piperazineethanesulfonic acid, HOBT refers to 1-hydroxybenzotriazole, HRP refers to horse raddish peroxidase, IGF refers to insulin growth factor, MOPS refers to 4-morpholinepropanesulfonic acid, MPS refers to multiple parallel synthesis, NMP refers to N-methyl formamide, OPD refers to o-Phenylenediamine, PBS refers to phosphate buffer saline, PKA refers to protein kinase A, PKB refers to protein kinase B, PKC refers to protein kinase C, rpm refers to rounds per minute, SAR refers to structure-activity relationship, THF refers to tetrahydrofuran, TIS refers to tri-isopropyl-silane, TFA refers to trifluoric acetic acid.

Pharmacology

The compounds of the present invention can be administered to a subject in a number of ways, which are well known in the art. Hereinafter, the term "subject" refers to the human or lower animal to whom compounds of the present invention are administered.

The novel pharmaceutical compositions of the present invention contain in addition to the active ingredient conventional pharmaceutically acceptable carriers, diluents and the like. Solid compositions for oral administration such as tablets, pills, capsules or the like may be prepared by mixing the active ingredient with conventional, pharmaceutically acceptable ingredients such as corn starch, lactose, sucrose, sorbitol, talc, stearic acid, magnesium stearate, dicalcium phosphate and gums with pharmaceutically acceptable diluents. The tablets or pills can be coated or otherwise compounded with pharmaceutically acceptable materials known in the art to provide a dosage form affording prolonged action or sustained release. Other solid compositions can be prepared as suppositories, for rectal administration. Liquid forms may be prepared for oral administration or for injection, the term including subcutaneous, transdermal, intravenous, intrathecal, and other parenteral routes of administration. The liquid compositions include aqueous solutions, with or without organic cosolvents, aqueous or oil suspensions, flavored emulsions with edible oils, as well as elixirs and similar pharmaceutical vehicles. In addition, the compositions of the present invention may be formed as aerosols, for intranasal and like administration. More preferred formulations include sustained release or depot formulations which may provide a steady state pharmacokinetic profile.

However, it is evident to the man skilled in the art that dosages would be determined by the attending physician, according to the disease to be treated, method of administration, patient's age, weight, contraindications and the like.

The compounds defined above are effective as inhibitors of protein kinase and can be used as active ingredients of pharmaceutical compositions for treatment of one, or simultaneously several, symptoms of the disorders defined above.

The compounds of the present invention are administered for the above defined purposes in conventional pharmaceutical forms, with the required solvents, diluents, excipients, etc. to produce a physiologically acceptable formulation. They can be administered by any of the conventional routes of administration.

It will be appreciated that the most appropriate administration of the pharmaceutical compositions of the present invention will depend on the type of disorder or disease being treated.

Chemistry:

Known inhibitors of protein kinases were used to perform a preliminary screen for PKB inhibition. Among these known protein kinase inhibitors, the known PKA inhibitor compound H-89 was unexpectedly found to inhibit PKB activity with an $IC_{50}$ of 2.4 $\mu$M, while inhibiting PKA activity with $IC_{50}$ of 48 nM and PKC activity with $IC_{50}$ of 31 $\mu$M.

The disclosed compounds of the present invention were identified following a structure-activity relationship study involving rational and combinatorial modification of N-[2-(p-bromocinnamylamino)ethyl]-5-isoquinolinesulfonamide also known as H-89 (Chijiwa et al. J. Biol. Chem. 265, 5267, 1990) as depicted in FIG. 1.

Some of the preferred compounds of the present invention may conveniently be prepared using solution phase synthesis methods. Other methods known in the art to prepare isoquinoline compounds like those of the present invention, can be used and are comprised in the scope of the present invention.

By way of exemplification of the principles of the present invention, a search for inhibitory PKB compounds focused on SAR studies of the H-89 molecule, as exemplified hereinbelow. This was followed by SAR study of additional known protein kinase inhibitors that were unexpectedly identified as PKB inhibitors.

A preferred embodiment according to the present invention has the general formula I:

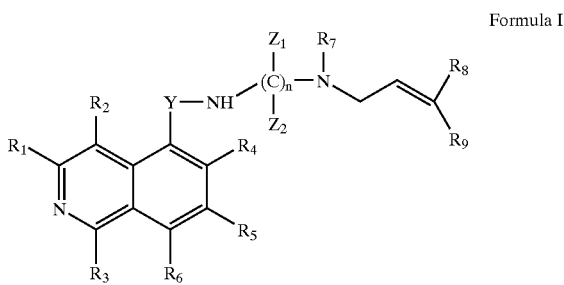

Formula I wherein:

$R_1$–$R_6$ are each independently selected from the group consisting of hydrogen, a lower alkyl group, a lower alkoxy group, a phenyl group, a lower alkyl substituted with at least one substituent selected from the group consisting of a phenyl group, a halogen, hydroxyl, thiol, nitro, cyano, or amino group;

Y is selected from the group consisting of sulfonyl, carbonyl, carbamate or carbamoyl;

$R_7$ is selected from the group consisting of hydrogen, a lower alkyl group, a lower alkoxy group, a phenyl group, a lower alkyl substituted with at least one substituent selected from the group consisting of a phenyl group, a halogen, hydroxyl, thiol, nitro, cyano, or amino group;

n is 1–2;

$Z_1$ and $Z_2$ are each independently hydrogen or a lower alkyl group;

$R_8$ and $R_9$ are each independently selected from the group consisting of a substituted or unsubstituted phenyl, alkylaryl, naphthyl, quinolyl or a halogen, with the proviso that at least one of $R_8$ and $R_9$ is aromatic.

One currently more preferred embodiment according to the present invention is the compound of Formula II:

Formula II

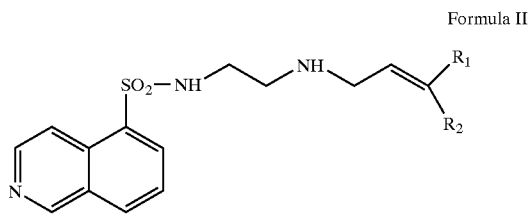

wherein $R_1$ and $R_2$ are independently selected from the group consisting of substituted or unsubstituted phenyl, alkylaryl, naphthyl, quinolyl, or a halogen, with the proviso that at least one of $R_1$ and $R_2$ is aromatic.

Another currently more preferred embodiment preferred of the present invention comprises a compound of Formula III:

Formula III

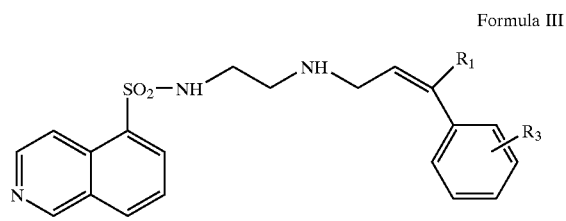

wherein $R_1$ is selected from the group consisting of substituted or unsubstituted phenyl, alkylaryl, naphthyl, quinolyl, or a halogen; and $R_3$ is selected from the group consisting of hydrogen, a lower alkyl group, a lower alkoxy group, substituted or unsubstituted phenyl group, a lower alkyl substituted with at least one substituent selected from the group consisting of a phenyl group, a halogen, hydroxyl, thiol, nitro, cyano, or amino group.

One currently most preferred embodiment of the present invention is the compound N1-(8-sulfonamide-5-isoquinoline)-N2-(3,3-diphenyl-2-propenyl)-ethylenediamine, denoted hereinbelow as B-11-1 of Formula IV:

Formula IV

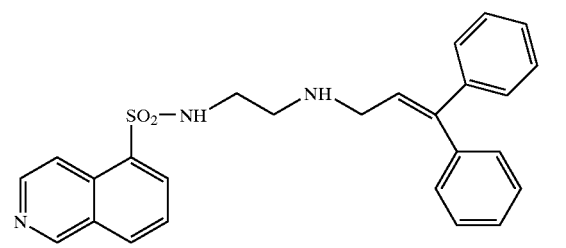

The currently most preferred embodiment disclosed in formula IV, inhibits 50% of PKB activity at a concentration of 3–4 $\mu$M (full inhibition at 20 $\mu$M) while its 50% inhibition of PKA activity occurs at a concentration of 9–10 $\mu$M. For the sake of comparison, the $IC_{50}$ values for protein kinase inhibition by the known compound H-89 are 2.4 $\mu$M for PKB and 50 nM for PKA.

There are biological experiments (example 4) indicates that this compound is capable of penetrating into cells. This characteristic makes it a preferred candidate for use as therapeutic composition.

This compound denoted B-11-1 includes an additional phenyl moiety and β substitution on the double bond adjacent to the phenyl moiety of H-89. These modifications contribute to its specificity.

The compound B-11-2, which is a N-dialkylated form of B-11-1 does not inhibit PKB activity and does not induce apoptosis, suggesting that the apoptosis induced by B-11-1 is mediated by PKB inhibition.

An additional most preferred embodiment of the present invention comprises a compound of Formula V:

Formula V

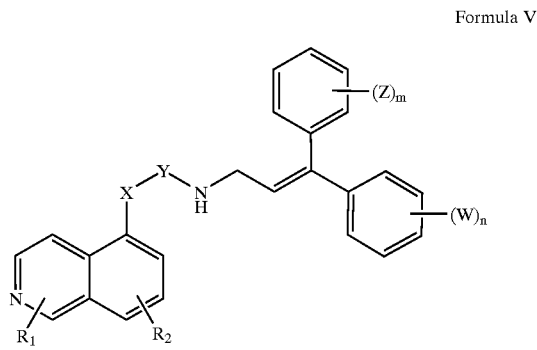

wherein:
X is selected from the group consisting of $SO_2$—NH, S and O;
Y represents substituted or unsubstituted alkylene of 1–4 carbons atoms;
$R_1$ and $R_2$ are independently selected from the group consisting of hydrogen, a lower alkyl group, a lower alkoxy group, substituted or unsubstituted phenyl group, a lower alkyl substituted with at least one substituent selected from the group consisting of a phenyl group, a halogen, hydroxyl, thiol, nitro, cyano, or amino group;
Z and W at each occurrence are independently selected from the group consisting of hydrogen, a halogen, $CF_3$, a lower alkoxy, OPhe, alkyl, substituted alkyl, phenyl or substituted phenyl;
m and n are each independently 0–4;
or, Z and W are connected via a bridge comprising 0–4 carbon atoms connected covalently through single or double bonds.

It is understood that if m or n is greater than 1 each substituent may be the same or different.

An example of a currently more preferred compound according to formula V is a compound of formula VI:

Formula VI

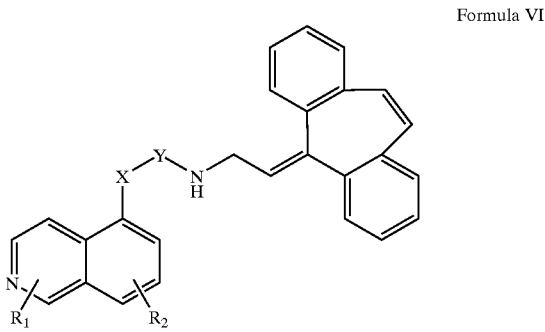

wherein:
X is selected from the group consisting of $SO_2$—NH, S and O;
Y represents substituted or unsubstituted alkylene of 1–4 carbons atoms;

$R_1$ and $R_2$ are independently selected from the group consisting of hydrogen, a lower alkyl group, a lower alkoxy group, substituted or unsubstituted phenyl group, a lower alkyl substituted with at least one substituent selected from the group consisting of a phenyl group, a halogen, hydroxyl, thiol, nitro, cyano, or amino group.

Protein kinases have more than one active site, as they possess a catalytic site for ATP and a substrate binding site. Additional preferred compounds according to the present invention can bind both sites at the same time and may have a synergistic effect that will give it unique potency and selectivity properties. These preferred compounds are chimeric molecules which are designed to include an ATP-mimetic molecule, connected via various spacers to a substrate-mimetic portion.

Biological Screening Assays for Inhibition of Protein Kinase Activity

Inhibition of Enzyme Activity in Cell Free system: PKA Activity Assay:

PKA activity is assayed on a 7-mer peptide, LRRASLG, known as kemptide. The assay is carried out in 96-well plates, in a final volume of 50 μl per well. The reaction mixture includes various concentrations of the inhibitor, 50 mM MOPS, 10 mM MgAc, 0.2 mg/ml BSA, 10 μM ATP, 20 μM Kemptide and 1 μCi γ$^{32}$P ATP. Reaction is started with addition of 15 μl of the catalytic subunit of PKA diluted in 0.1 mg/ml BSA, 0.4 U/well. Two blank wells without enzyme are included in every assay. The plates are agitated continuously at 30° C. for 10'. Reaction is stopped by addition of 12 μl 200 mM EDTA. 20 μl aliquots of the assay mixture are spotted onto 2 cm$^2$ phosphocellulose strips (e.g. Whatman P81) and immersed in 75 mM phosphoric acid (10 ml per sample). The phosphocellulose strips are washed 6 times. Washes are done in continuous swirling for 5 minutes last wash is in acetone. After air drying the strips, radiation is measured by scintillation spectrometry. Screening of libraries is done in duplicates with a single concentration of the inhibitor (5 μM). purified compounds are checked in various concentrations and their $IC_{50}$ value is determined.

Inhibition of Enzyme Activity in Cell Free System: PKB Activity Assay:

PKB activity is assayed as described in Alessi et al. (FEBS Letters 399, 333, 1996) with the following modifications: instead of HA-PKB coupled to beads, soluble His-HA-PKB is used following precipitation on a Nickel column. The enzyme activity measurement is performed as described in the assay for PKA.

Assays for Inhibition of PKB Activity in Intact Cells:

Several cancer cell lines were used to determine the activity of PKB inhibitors in intact cells. For example OVCAR3 is a cell line of ovarian carcinoma with an amplification of the PKB gene, U87MG is a glioma cell line with a deletion of PTEN gene—causing high activity of PKB, and PANC1 is a pancreatic carcinoma cell line with an amplification of PKB gene.

a. Annexin-V Assay for Apoptosis:

OVCAR3 cells were seeded in 10 cm plates (2×10$^6$ cells/plate) and treated with different concentrations of the inhibitor. 40 hours after treatment cells were trypsinysed, washed twice with PBS and suspended in annexin-V buffer annexin-V (Roche) is diluted 1:250 in a buffer containing 10 mM HEPES pH 7.4, 140 mM NaCl, 5 mM $CaCl_2$ and 0.2 nM propidium iodid (PI). Apoptosis measurement was performed by FACS analysis.

b. Growth Inhibition:

OVCAR3, U87MG and PANC1 cells were seeded in 96-well plates. In each plate cells were treated with different concentrations (0, 5, 10, 25, 50, 75, 100 μM) of the inhibitor, in triplicates. Every day one plate was fixed by 0.5% gluterdialdehyde, and the inhibitor was replaced in the rest of the plates. After fixation the cells were stained with methylene-blue 1% for one hour. Plates were washed with distilled water and dried. Extraction of color was performed by adding 0.1 M HCl for one hour at 37° C. Quantitation of color intensity was performed by measurement of the optical density at 620 nm by ELISA reader.

c. Inhibition of Phosphorylation:

Cells were seeded in 6-well plates, and treated with different concentrations of the inhibitor. Treatment was taken either under serum containing media or under starvation for different time periods. After treatment cells are stimulated for 10' with IGF-1 (HEK-293 and PANC1 cells) or EGF (OVCAR3 and U89MG cells). Cell lysates are prepared using boiled sample buffer. Western blot analysis with a phospho-GSK3 showed decrease in GSK3 phosphorylation. The effect was also tested on GSK3 phosphorylation by expression of kinase-dead-PKB in 293 cells.

Transfer ELISA Assay for Measuring PKB Activity and Inhibition.

The inhibitor tested is dissolved in water to the desired concentration. Five μl of the inhibitor solution is added to the wells of a V shaped polypropylene microplate. Five μl of substrate peptide (Biotin-Lys-Gly-Arg-Pro-Arg-Thr-Ser-Ser-Phe-Ala-Glu-Gly) (SEQ ID NO. 3) solution in water at a concentration of 300 μM is then added to the wells (final assay concentration is 100 μM). Then PKB enzyme dissolved in 3× reaction mixture (50 mM Tris HCl pH 7.5, 0.1% beta mercaptoethanol, 1 μM PKI (Calbiochem), 10 mM Mg acetate, ATP 5 μM), is added in pre-calibrated amount to the wells. The amount of enzyme is calibrated so that less than 10% of the substrate is phosphorylated by the end of the reaction as evaluated by mass spectral analysis. The plate is covered with an adhesive tape, placed over a 1 mm ID vortex at 30° C. and incubated for 30 min to 1 hour as needed. At the end of the incubation period 5 μl of 0.5 M disdium EDTA are added to the wells followed by 180 μl of PBS.

For ELISA, a microplate (Costar A/2) is coated with 20 μl of 10 μg/ml of avidin in PBS (over night at 4° C. or 30 minutes at 37° C., on a 1 mm ID vortex). The plate is than washed several times with dionized water and flicked dry on a towel paper. The wells are filled with 20 μl of PBT (PBS+1% BSA+0.05% tween 20). Five μl from the enzyme reaction plate are transferred to the ELISA plate. The ELISA plate in placed on the 1 mm ID vortex and incubated for 10 min at RT. The plate is than washed with water as before. To each well 20 μl of anti phosphopeptide antibody (Cell Signaling Technology) diluted 1:1000 in PBT are added. The plate is placed again on the vortex, incubated for 30 minutes and washed with water as before. To each well 20 μl of goat anti-rabbit Ig conjugate with horse raddish peroxidase (HRP) is added. The plate is placed on the vortex, incubated for 20 min and washed with water as before. To each well is added 20 μl of HRP substrate (Sigmafast OPD). After sufficient color development (up to maximum of about 30 minutes development time) the reaction is terminated by the addition of 20 μl per well of 4 M HCl in water. The plate is than read using an ELISA reader at 490 nm. The signal obtained from wells containing potential inhibitors is compared to signal obtained from wells containing only the enzyme without inhibitor (maximum signal) and wells not containing enzyme (minimum signal).

The fraction of phosphorylated peptide can be also analyzed by mass spectra following desalting on a ziptip (C18, Millipore i). Mass of double charged substrate peptide is 759.3 Dalton, and of the double charged phosphorylated peptide is 799.3 Dalton.

EXAMPLES

Example 1

Screening PKA Inhibitors for PEB Inhibition

Since there are no known inhibitors of PKB, the structural similarity between PKB and other protein kinases was used to screen commercially available inhibitors of other protein kinases, e.g., PKA and PKC, for PKB inhibition. The preliminary screen was conducted in order to define some structural motifs in active compounds that would assist in the initial design of a combinatorial library of candidate compounds.

It should be noted, however, that though this approach is very useful for rapid identification of lead molecules, the molecules that are identified would possess inhibition activity against other kinases as well. Thus, this approach dictates research directed not only at optimization of the inhibitory activity, but also, and perhaps most importantly, specificity-oriented research. Namely, substantial efforts are actually directed at modifying the selectivity profile, in order to obtain a profile of selectivity or specificity towards PKB.

The screen yielded two compounds that inhibited PKB in the 2–3 $\mu$M range. H-89, a known PKA inhibitor, was chosen to be the basic scaffold for the design of the first library, based on its structure and on synthetic and specificity considerations.

Example 2

Modification of H-89 for Identification of PKB Inhibitors

The structure of H-89 makes it an ideal candidate for SAR study using combinatorial chemistry, since it allows diversity in many regions of the molecule. The isoquinoline moiety could be replaced with various bicyclic and aromatic residues, the ethylenediamine bridge can vary in length, hydrogen bonding properties and substitution, and the cinnamoyl moiety can be modified to a large variety of structures for the evaluation of the optimal properties of this region. In addition, the sulfonamide group can be replaced with carbonyl and other similar moieties. FIG. 1 shows the various regions of diversity in the structure of H-89 which were used to construct combinatorial libraries. The libraries were designed to explore each region's contribution to the inhibition potency and to the specificity against other kinases.

Region A. A diversity of bicyclic cores, and aromatic heterocyclic cores.

Region B. A diversity of spacers modified in length, electrostatic properties and substitutions.

Region C. A diversity of "tails", either aliphatic or aromatic, differing in length, electrostatic and steric properties.

Region D. Replacement of the sulfonamide with a carboxy amide, urea, amine, a simple methylene, etc.

H-89 analogs for SAR study were synthesized in parallel in 96-well format using solution chemistry. The first library studied region C and examined the necessity of an aromatic residue in that area Four bicyclic cores were used in this plate, thus each of the aliphatic moieties that were studied, was tested with the original 5-isoquinoline core, and three other alternative bicyclic systems. The four different A cores were coupled each with 16 different B+C modified regions and screened in-vitro for inhibition of PKA and PKB enzyme activity. No activity was observed in this library, including the compounds containing 5-isoquinoline moiety and resembling H-89 in all features except the presence of an aromatic residue. The conclusion was that interaction with a highly hydrophobic feature in the C region is very important, and the next libraries were designed accordingly.

Before designing the next library, a miniseries of 9 compounds aimed at optimization of the chemistry of the bond connecting regions B and C, was synthesized. An amine bond (as in H-89) and an amide bond were synthesized and compared, for three different bicyclic A cores and three different C regions. The compounds are depicted in FIG. 2, together with the $IC_{50}$ for PKB inhibition.

The results of the miniseries clearly show that an amide bond is less favorable for the inhibition of PKB than an amine. It also implies that either the length of the chain connecting the aromatic residue of part C to the amine, or the presence of a double bond in it, is also significant, although the effect seems less pronounced than the conversion of the amine to an amide. Based on these results, we turned to design the next several libraries. They were all based on an amine bond connecting part C and B, and an aromatic residue in part C.

The diversity regions examined in the next libraries were the core A, the length and type of the diamino bridge B, and the tail C. These modifications were studied in three different libraries:

i. Several cores in region A and a diversity of substitutions at region C.

ii. Several diamino bridges at region B and a diversity of substitutions at region C.

iii. Additional region A cores studied with a limited number of region C substitutions.

All libraries were screened for both PKB and PKA inhibition, to assess the contribution of each structural modification to the activity of either enzyme. As discussed before, since the initial lead is a known PKA antagonist, the SAR should be directed mainly at identifying the specific enzyme-ligand interactions, which are not common to both PKA and PKB. Naturally, finding these non-mutual interactions will assist in designing more potent and selective PKB inhibitors.

For example, it would be desirable to identify structural features which are essential for the PKA inhibition but that have little no effect on PKB inhibition, and use them to improve the desired selectivity. In other words, these essential structural features may be altered, thereby decreasing the PKA inhibitory activity without adversely affecting the PKB inhibitory activity.

Analysis of the SAR results clearly shows that at region A, none of the cores that were tested worked, except of the 5-isoquinoline. Replacement with any other core, either as a sulfonamide or a carboxamide derivative, eliminated activity. On region B, elongation of the bridge from two to three carbons diminished activity, as did substitution on the chain. Using cyclic secondary amine derivatives resulted in elimination of the activity in the case of homopiperazine, implying that the amino protons are important to the interaction, possibly through hydrogen bonding. Surprisingly, the piperazine derivatives showed activity, but significantly less pronounced than the corresponding ethylenediamine analogs.

Figure 3:
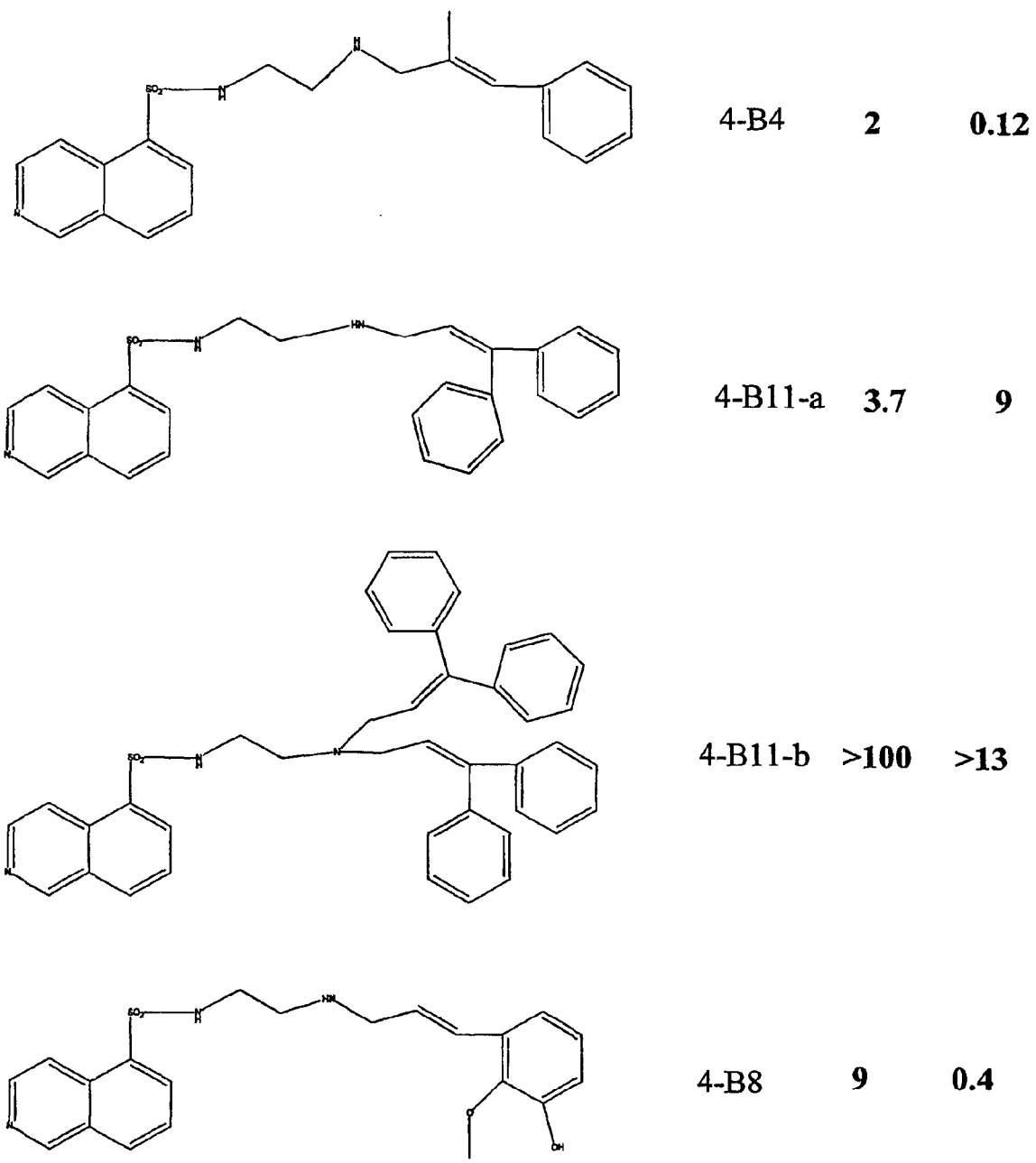

The most significant SAR was observed in the diversity of moieties used for region C. The results show that activities of compounds derived from 5-isoquinoline-sulfonamide-ethylenediamine, with various moieties at region C, vary from almost no activity to very significant activities. Notably, significant variation was observed also in the activity of PKA. In several cases, the inhibition of PKA was significantly decreased. Several of the active compounds from the library were selected for re-synthesis, purification and full characterization, and $IC_{50}$ values for inhibition of PKA and PKB were determined. The results are compiled in FIG. 3.

As discussed before, identifying non-mutual interactions was important for the design of specific inhibitors. The SAR results depicted in FIG. 3 indicate that an additional bulky substitution at the carbon bearing the aromatic residue in region C, is unfavorable for PKA inhibition, but has a negligible effect on PKB inhibition. To verify this conclusion, we synthesized a series of compounds bearing such a bulky substitution, and some representative results are depicted in FIG. 4 (the results are represented either as $IC_{50}$ values or as percent inhibition). The results demonstrate that molecules with additional hydrophobic substitution next to the aromatic residue in region C showed significant decrease in PKA inhibition, and a very small effect on PKB inhibition. These results confirm that this position is indeed a PKA "irritant", shifting its $IC_{50}$ value for 50 nM to several $\mu$M, while its effect on PKB is minor. The identification of this feature is crucial to the further optimization of the disclosed compounds. Since the two enzymes are so similar, a major potential problem is that any modification we make that will improve affinity for PKB, will probably have the same effect on PKA. However, by having the ability to introduce a bulky substitution at the identified position we can selectively decrease the activity of PKA with only negligible effects on the activity of PKB.

Example 3

Detailed Synthesis of the Lead Compound B-11-1

The following is an example of a method of manufacturing the compound B-11-1.
(1) 5-isoquinoline N-(3-aminoethyl)sulfonamide One gr. (4.7 mMole) of 5-isoquinoline sulfonic acid were dissolved in 0.5 ml of DMF and added 4.6 ml (13 equivalents) of thionyl chloride. The mixture was refluxed for 2 hours, cooled and evaporated to dryness. The residue was added very slowly to a pre-cooled (0°) flask containing 3.6 ml (10 equivalents) of ethylene diamine in methylene chloride. The reaction was stirred at RT for 6 hrs. workup was done by extraction with Water and chloroform, and the organic layer was evaporated and chromatographed on silica using 5%–15% gradient of methanol in chloroform. Clean product was obtained in 35% yield. MS: 252, NMR: 2.64(t, 2) 2.917(t, 2) 7.81(t, 1) 8.38(d, 1) 8.45(d, 1) 8.61(d, 1) 9.3(s, 1).
(2) N1-(8-sulfonamide-5-isoquinoline)-N2-(3,3-diphenyl-2-propenyl)-ethylenediamine, denoted B-11-1

Twenty five mg of 5-isoquinoline N-(3-aminoethyl) sulfonamide (1) were dissolved in methanol and added 64 mg of $NaBCNH_3$ and a trace of acetic acid. (approx. 1%). After 5 minutes of stirring, 19 mgs of diphenyl cinnamaldehyde were added, and the reaction was stirred for 3 hrs. Workup was dine by addition of basic water ($NaHCO_3$) and chloroform and extraction. The organic layer was evaporated and chromatographed on silica with 3% methanol in methylene chloride. The purified product (NL-71-101-b) was obtained in 65% yield.

Example 4

Further Biological Evaluation of B-11-1

The best compound derived from the exemplary SAR study disclosed hereinabove was B11-1. This compound exhibits greater selectivity toward PKB than the original compound H-89, since its potency in inhibiting PKA activity is about 330 times lower. The results of enzyme inhibition in the cells-free assay by both compounds are summarized in table 1.

TABLE 1

| Inhibition of PKA and PKB enzyme activity ($\mu$M). | | |
|---|---|---|
| Enzyme | Compound | |
| inhibited | B-11-1 | H-89 |
| PKB | 3.7 | 1.4 |
| PKA | 8.6 | 0.026 |

B-11-1 was further characterized and tested for inhibition of PKB in additional assays:

B11-1 potency for inhibition of PKB activity in whole cells determined as induction of apoptosis was measured in the Annexin-V assay. The results of the effects of are summarized in table 2:

TABLE 2

| Induction of apoptosis by B-11-1 | | | | | |
|---|---|---|---|---|---|
| treatment | 0 | vehicle | 25 $\mu$M | 50 $\mu$M | 75 $\mu$M | 100 $\mu$M |
| % apoptosis | 10 | 12 | 11 | 19 | 42 | 64 |

Figure 5A:
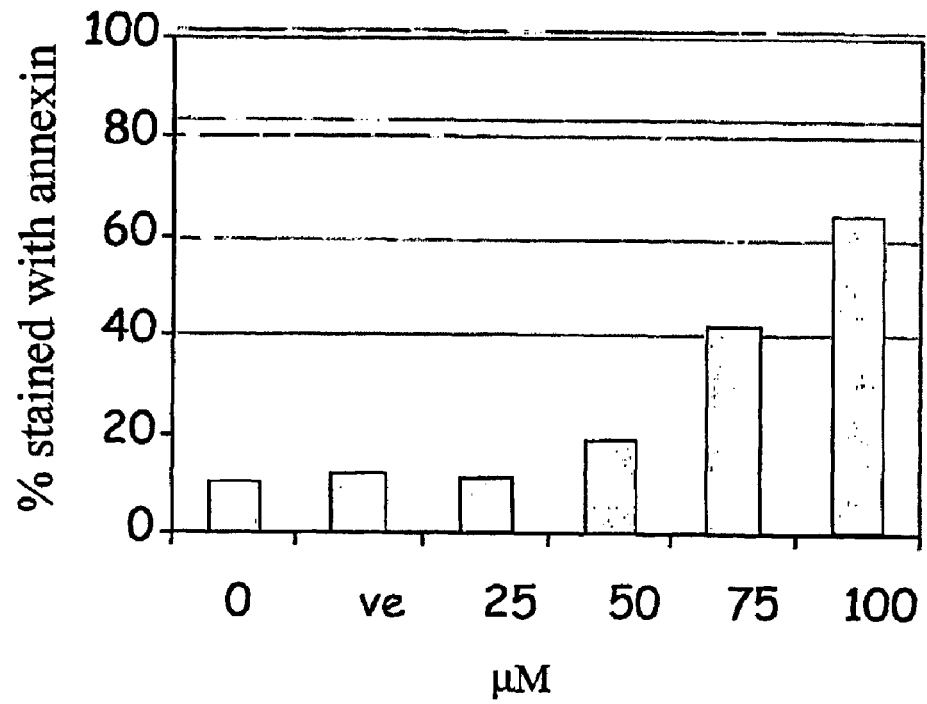
FIG. 5. The effects of compounds B-11-1 (A) and B-11-2 (B) on OVCAR3 cell apoptosis determined by staining with annexin.
Figure 5B:
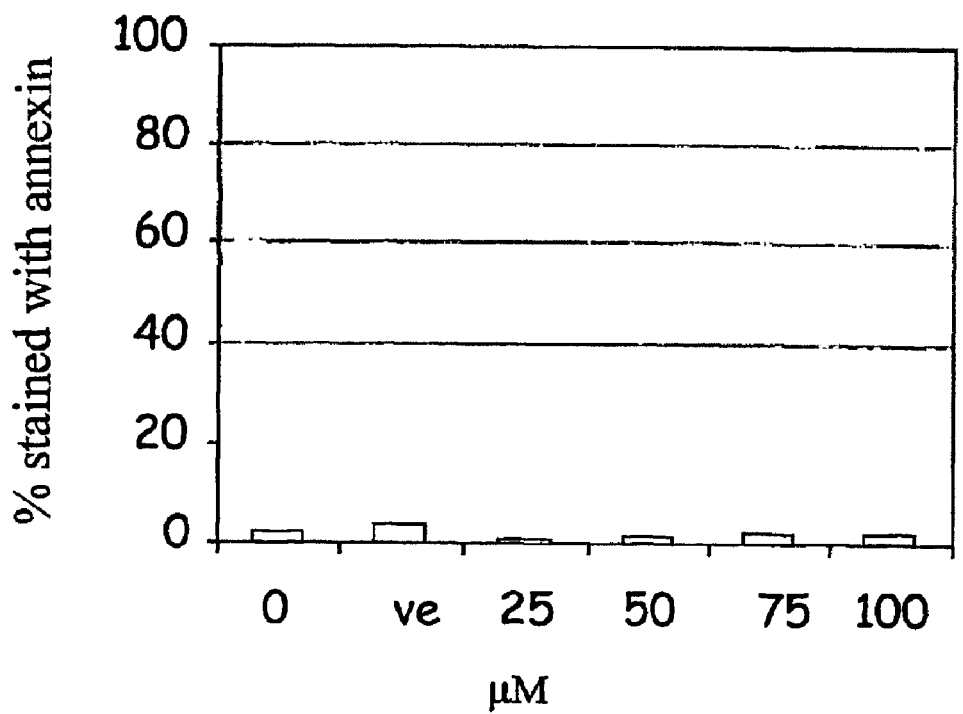

The compound B-11-2, which is an N-dialkylated form of B-11-1 and does not inhibit PKB in-vitro, did not induce apoptosis as described in FIG. 5B, suggesting that the apoptosis induced by B11-1 (FIG. 5A) is mediated by PKB inhibition.

The activity of B-11-1 was also determined by cells growth inhibition assay in OVCAR3 and U87MG cells. The compound was tested in concentrations of 0, 5, 10, 25, 50, 75, 100 $\mu$M. The results showed that concentrations of 75 and 100 $\mu$M were lethal for the cells after 48 hours. 50 $\mu$M were lethal after 72 hours, while 25 $\mu$M and lower concentration had minimal effects. The two high concentrations also had lethal effects on PANC1 cells after 48 hours treatment. $IC_{50}$ for growth inhibition of PANC1 cells was determined after 72 hours treatment. The $IC_{50}$ found was around 30 $\mu$M.

B-11-1 exhibits inhibition of PKB activity in intact cells as determined by western blot analysis with a phospho-GSK3. The results showed decrease in GSK3 phosphorylation at compound concentration of 100 $\mu$M. Similar effect on GSK3 phosphorylation was observed by expression of kinase-dead-PKB in 293 cells.

Example 5

Improvement of B-11-1

Twenty-four compounds designed for improvement of the activity of B-11-1, including modifications in region C and D (sulfone substituted by ether), were synthesized. The structures are presented in the Table 3:

TABLE 3
Structure
EN-118-105-4
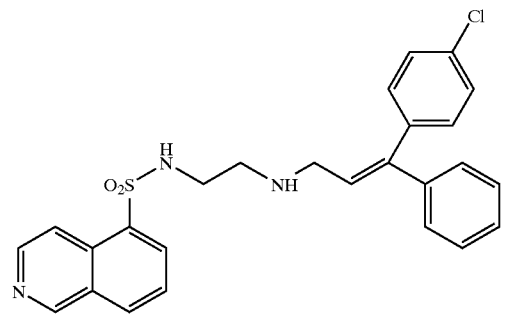
EN-118-105-5e
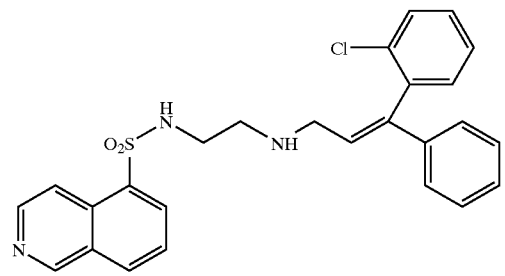
EN-118-107-1
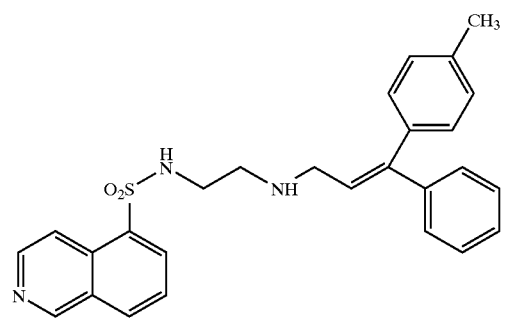
EN-118-107-2
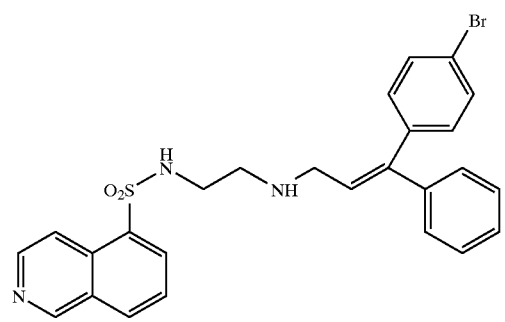
TABLE 3-continued
Structure
EN-118-107-7
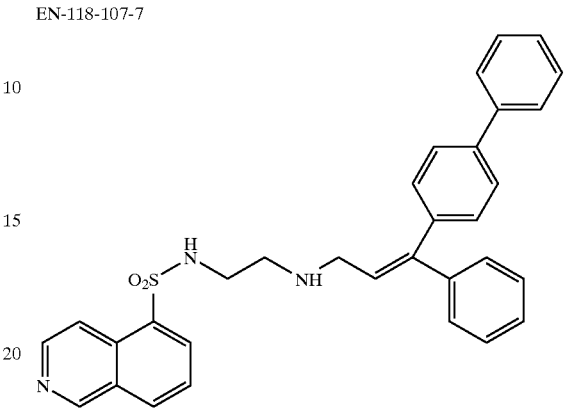
EN-118-107-8
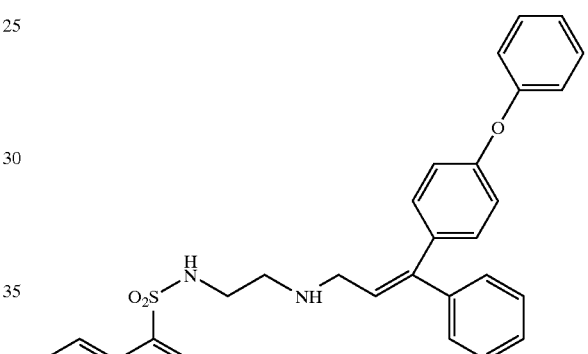
EN-118-107-9
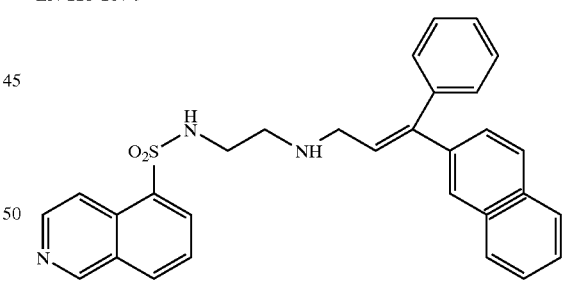
EN-118-97-2
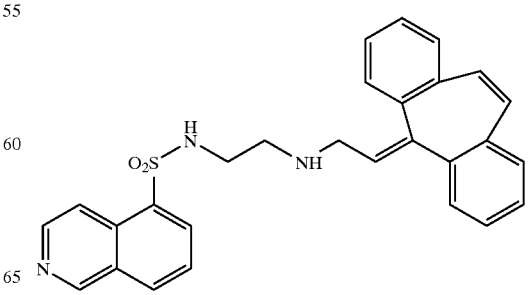

TABLE 3-continued
Structure
EN-118-97-4
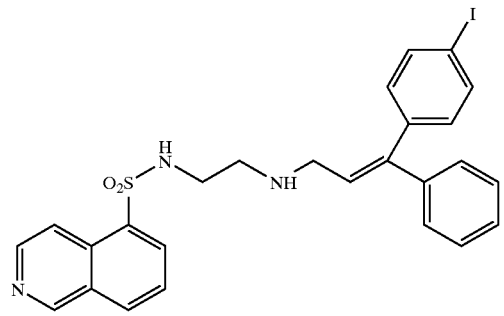
EN-118-97-5
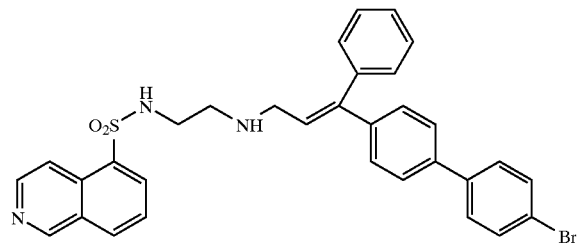
PTR 6026
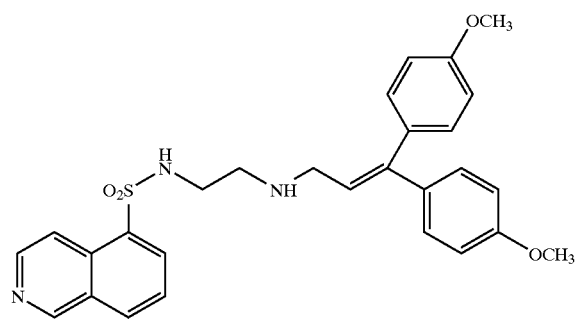
PTR 6028
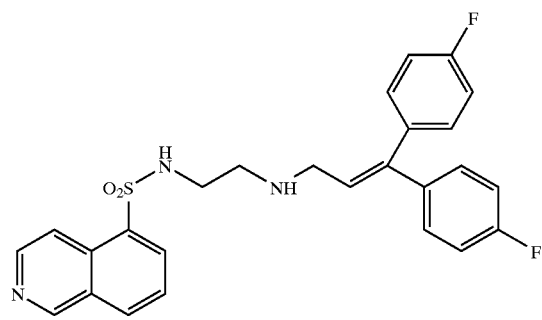
TABLE 3-continued
Structure
PTR 6032
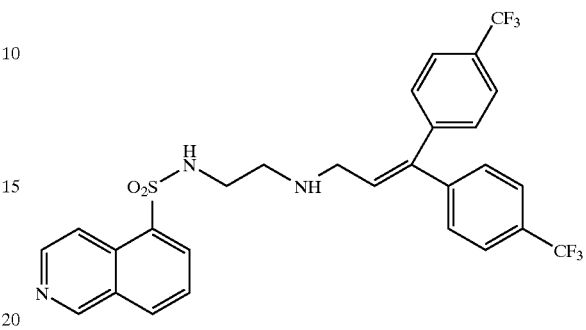
PTR 6034
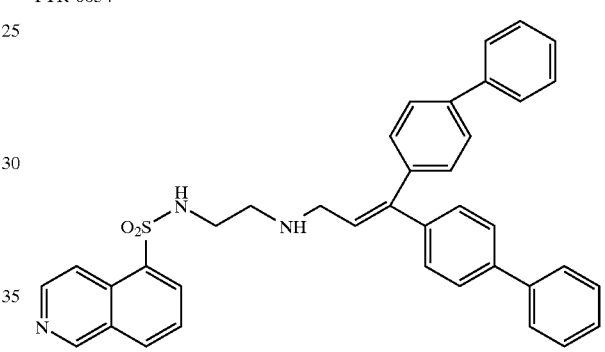
PTR 6036
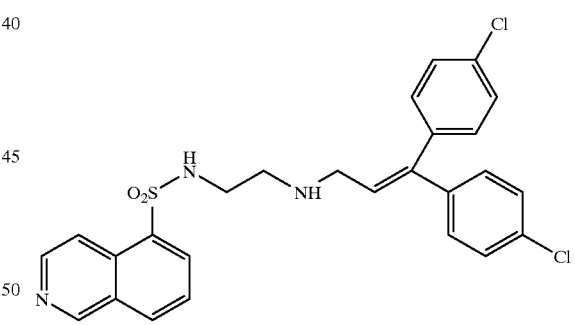
PTR 6038
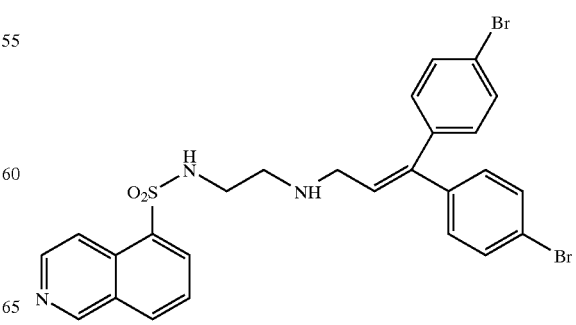

TABLE 3-continued

Structure

PTR 6040

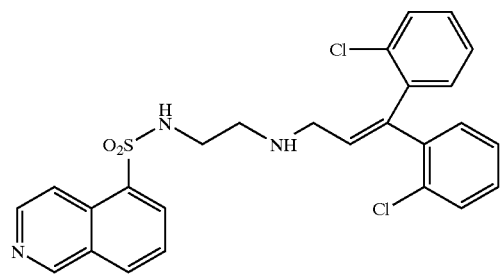

PTR 6042

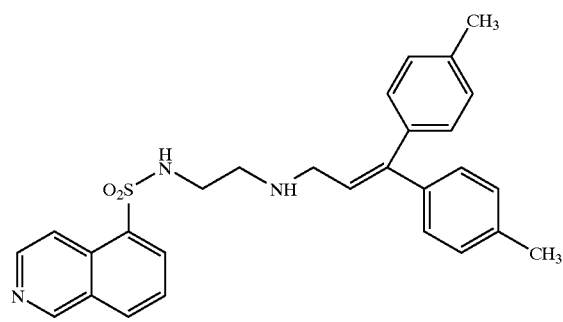

PTR 6044

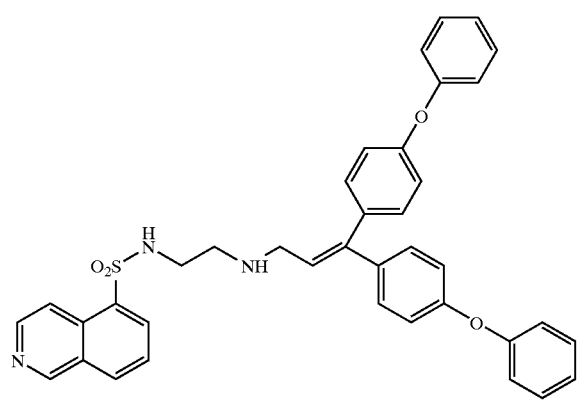

NL-71-161a

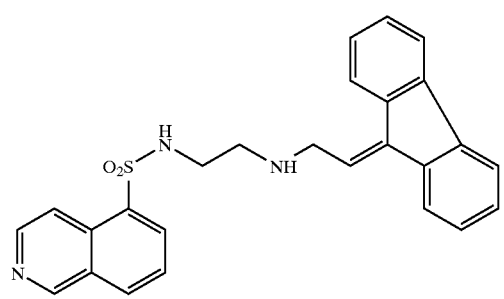

TABLE 3-continued

Structure

NL-71-159a

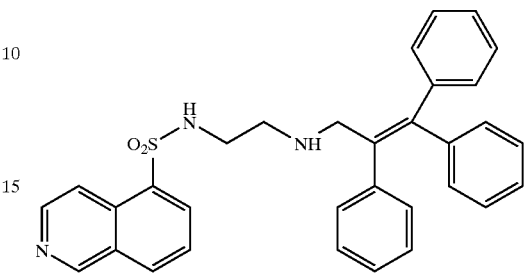

EN-118-19

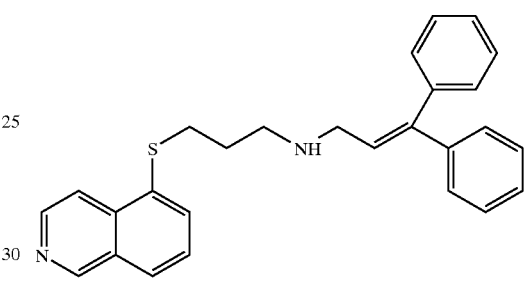

EN-118-29

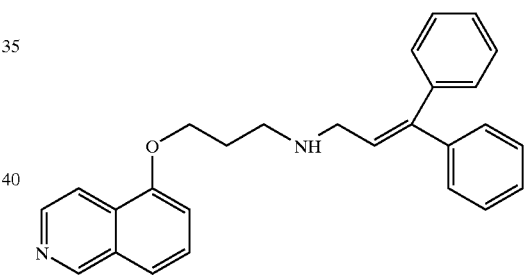

EN-118-115-4

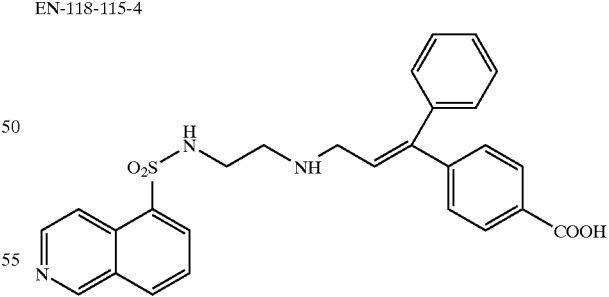

The skilled artisan will appreciate that the above examples are merely illustrative and serve as non limitative exemplification of the principles of the present invention and that many variations and modifications are possible within the scope of the currently claimed invention as defined by the claims which follow.

What is claimed is:

1. A compound having general Formula I:

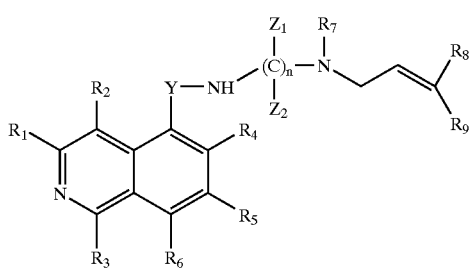

Formula I wherein:

$R_1$–$R_6$ are each independently selected from the group consisting of hydrogen, a lower alkyl group, a lower alkoxy group, a phenyl group, a lower alkyl substituted with at least one substituent selected from the group consisting of a phenyl group, a halogen, hydroxyl, thiol, nitro, cyano, or amino group;

Y is selected from the group consisting of sulfonyl, carbonyl, carbamate or carbamoyl;

$R_7$ is selected from the group consisting of hydrogen, a lower alkyl group, a lower alkoxy group, a phenyl group, a lower alkyl substituted with at least one substituent selected from the group consisting of a phenyl group, a halogen, hydroxyl, thiol, nitro, cyano, or amino group;

n is 1–2;

$Z_1$ and $Z_2$ are each independently hydrogen or a lower alkyl group;

$R_8$ and $R_9$ are each independently selected from the group consisting of a substituted or unsubstituted phenyl, alkylaryl, naphthyl, quinolyl or a halogen, wherein least one of $R_8$ and $R_9$ is aromatic.

2. The compound of claim 1, wherein $R_1$–$R_6$ are hydrogen.

3. The compound claim 1, wherein the structural formula of the compound is represented by Formula II:

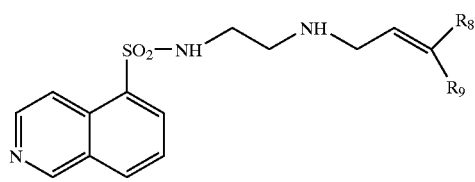

Formula II wherein:

$R_8$ and $R_9$ are independently selected from the group consisting of substituted or unsubstituted phenyl, alkylaryl, naphthyl, quinolyl, or a halogen, with the proviso that at least one of $R_8$ and $R_9$ is aromatic.

4. The compound of claim 3 wherein $R_8$ and $R_9$ are each independently an aromatic group.

5. The compound of claim 1, wherein the structural formula of the compound is represented by Formula III:

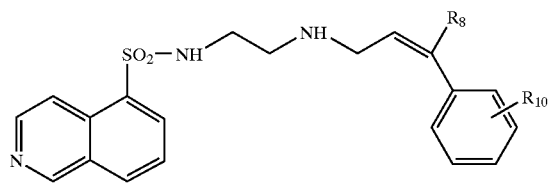

Formula III wherein $R_8$ is selected from the group consisting of substituted or unsubstituted phenyl, alkylaryl, naphthyl, quinolyl, or a halogen; and $R_{10}$ is selected from the group consisting of hydrogen, a lower alkyl group, a lower alkoxy group, substituted or unsubstituted phenyl group, a lower alkyl substituted with at least one substituent selected from the group consisting of a phenyl group, a halogen, hydroxyl, thiol, nitro, cyano, or amino group.

6. The compound of claim 5, wherein $R_8$ is phenyl and $R_{10}$ is H.

7. A compound of general Formula V:

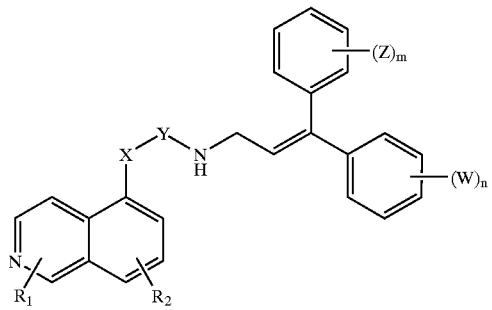

Formula V wherein:

X is selected from the group consisting of $SO_2$—NH, S and O;

Y represents substituted or unsubstituted alkylene of 1–4 carbons atoms;

$R_1$ and $R_2$ are independently selected from the group consisting of hydrogen, a lower alkyl group, a lower alkoxy group, substituted or unsubstituted phenyl group, a lower alkyl substituted with at least one substituent selected from the group consisting of a phenyl group, a halogen, hydroxyl, thiol, nitro, cyano, or amino group;

Z and W at each occurrence are independently selected from the group consisting of H, F, Cl, Br, I, $CF_3$, $OCH_3$, OPhe, alkyl, substituted alkyl, phenyl or substituted phenyl;

m and n are each independently 0–4;

or, Z and W are connected via a bridge comprising 0–4 carbon atoms connected covalently through single or double bonds.

8. The compound of claim 7 wherein Z and W are connected by a bridge comprising 0 to 4 carbon atoms, and the compound is represented by Formula VI:

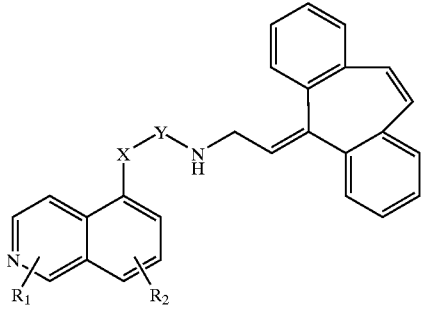

Formula VI wherein:

X is selected from the group consisting of $SO_2$—NH, S and O;

Y represents substituted or unsubstituted alkylene of 1–4 carbons atoms;

$R_1$ and $R_2$ are independently selected from the group consisting of hydrogen, a lower alkyl group, a lower alkoxy group, substituted or unsubstituted phenyl group, a lower alkyl substituted with at least one substituent selected from the group consisting of a phenyl group, a halogen, hydroxyl, thiol, nitro, cyano, or amino group.

9. A pharmaceutical composition comprising as an active ingredient a compound of general Formula V

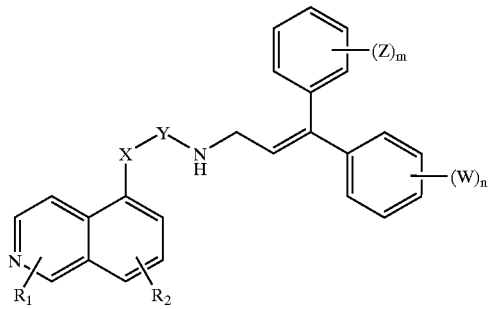

Formula V wherein:
X is selected from the group consisting of SO$_2$—NH, S and O;
Y represents substituted or unsubstituted alkylene of 1–4 carbons atoms;
$R_1$ and $R_2$ are independently selected from the group consisting of hydrogen, a lower alkyl group, a lower alkoxy group, substituted or unsubstituted phenyl group, a lower alkyl substituted with at least one substituent selected from the group consisting of phenyl group, a halogen, hydroxyl, thiol, nitro, cyano, or amino group;
Z and W at each occurrence are independently selected from the group consisting of H, F, Cl, Br, I, CF$_3$, OCH$_3$, OPhe, alkyl, substituted alkyl, phenyl or substituted phenyl;
m and n are each independently 0–4; or, Z and W are connected via a bridge comprising 0–4 carbon atoms connected covalently through single or double bonds.

10. The pharmaceutical composition of claim 9, wherein $R_1$–$R_2$ are hydrogen.

11. The pharmaceutical composition of claim 9, wherein the Z and W are connected by a bridge comprising 0 to 4 carbon atoms, and the compound is represented by Formula VI:

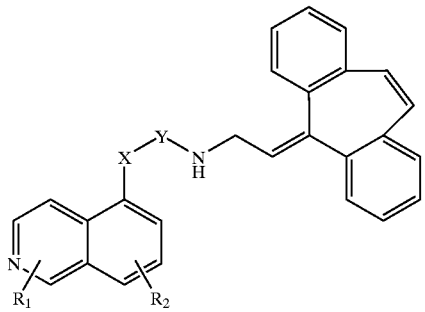

Formula VI wherein:
X is selected from the group consisting of SO$_2$—NH, S and O;
Y represents substituted or unsubstituted alkylene of 1–4 carbons atoms;
$R_1$ and $R_2$ are independently selected from the group consisting of hydrogen, a lower alkyl group, a lower alkoxy group, substituted or unsubstituted phenyl group, a lower alkyl substituted with at least one substituent selected from the group consisting of phenyl group, a halogen, hydroxyl, thiol, nitro, cyano, or amino group.

12. A pharmaceutical composition comprising as an active ingredient a compound of general Formula I:

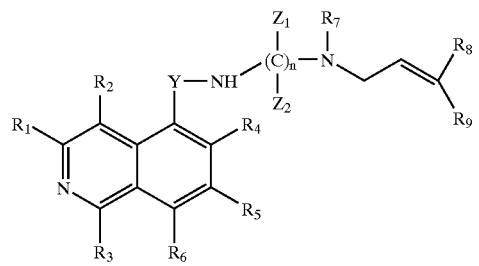

Formula I wherein
$R_1$–$R_6$ are each independently selected from the group consisting of hydrogen, a lower alkyl group, a lower alkoxy group, a phenyl group, a lower alkyl substituted with at lest one substituent selected from the group consisting of a halogen, hydroxyl, thiol, nitro, cyano, or amino group;
Y is selected from the group consisting of sulfonyl, carbonyl, carbamate or carbamoyl;
$R_7$ is selected from the group consisting of hydrogen, a lower alkyl group, a lower alkoxy group, a phenyl group, a lower alkyl substituted with at lest one substituent selected from the group consisting of a halogen, hydroxyl, thiol, nitro, cyano, or amino group;
n is 1–2;
$Z_1$ and $Z_2$ are each independently hydrogen or a lower alkyl group;
$R_8$ and $R_9$ is each independently selected from the group consisting of a substituted or unsubstituted phenyl, alkylaryl, naphthyl, quinolyl or a hydrogen, wherein at least one of $R_8$ and $R_9$ is aromatic.

13. The pharmaceutical composition of claim 12, wherein the compound is in the form of a compound of Formula II

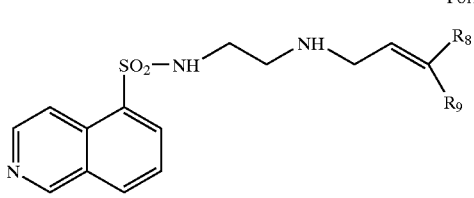

Formula II wherein $R_8$ and $R_9$ are independently selected from the group consisting of substituted or unsubstituted phenyl, alkylaryl, naplithyl, quinolyl, or a halogen, wherein at least one of $R_8$ and $R_9$ is aromatic, and the pharmaceutical composition further comprises a pharmaceutically acceptable diluent or carrier.

14. The pharmaceutical composition of claim 13, wherein $R_8$ and $R_9$ are each independently an aromatic group.

15. The pharmaceutical composition of claim 12, wherein the active ingredient is a compound is in the form of Formula III:

Formula III

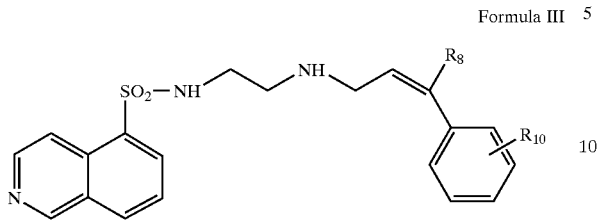

wherein:

$R_8$ is selected from the group consisting of substituted or unsubstituted phenyl, alkylaryl, naphthyl, quinolyl, or a halogen; and $R_{10}$ is selected from the group consisting of hydrogen, a lower alkyl group, a lower alkoxy group, substituted or unsubstituted phenyl group, a lower alkyl substituted with at least one substituent selected from the group consisting of phenyl group, a halogen, hydroxyl, thiol, nitro, cyano, or amino group.

16. The pharmaceutical composition of claim 15, wherein $R_8$ is phenyl and $R_{10}$ is H.

17. A method for inhibiting a protein kinase B in a subject, wherein the method comprises administering to a patient in need thereof a compound having general Formula I or general formula V, wherein general Formula I is Formula I

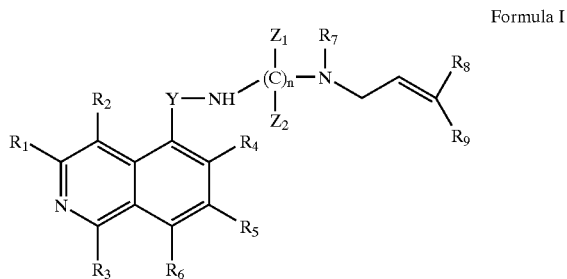

wherein $R_1$–$R_6$ are each independently selected from the group consisting of hydrogen, a lower alkyl group, a lower alkoxy group, a phenyl group, a lower alkyl substituted with at lest one substituent selected from the group consisting of a halogen, hydroxyl, thiol, nitro, cyano, or amino group;

Y is selected from the group consisting of sulfonyl, carbonyl, carbaniate or carbamoyl;

$R_7$ is selected from the group consisting of hydrogen, a lower alkyl group, a lower alkoxy group, a phenyl group, a lower alkyl substituted with at lest one substituent selected from the group consisting of a halogen, hydroxyl, thiol, nitro, cyano, or amino group;

n is 1–2;

$Z_1$ and $Z_2$ are each independently hydrogen or a lower alkyl group;

$R_8$ and $R_9$ is each independently selected from the group consisting of a substituted or unsubstituted phenyl, alkylaryl, naphthyl, quinolyl or a halogen, wherein at least one of $R_8$ and $R_9$ is aromatic, and general Formula V is Formula V

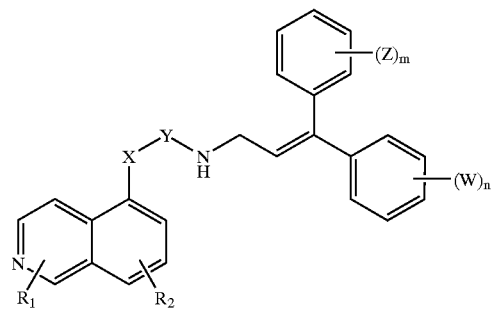

wherein:

X is selected from the group consisting of $SO_2$—NH, S and O;

Y represents substituted or unsubstituted alkylene of 1–4 carbons atoms;

$R_1$ and $R_2$ are independently selected from the group consisting of hydrogen, a lower alkyl group, a lower alkoxy group, substituted or unsubstituted phenyl group, a lower alkyl substituted with at least one substituent selected from the group consisting of phenyl group, a halogen, hydroxyl, thiol, nitro, cyano, or amino group;

Z and W at each occurrence are independently, selected from the group consisting of H, F, Cl, Br, I, $CF_3$, $OCH_3$, OPhe, alkyl, substituted alkyl, phenyl or substituted phenyl;

m and n are each independently 0–4; or, Z and W are connected via a bridge comprising 0–4 carbon atoms connected covalently through single or double bonds.

18. The method of claim 17, wherein the compound is a compound of general formula I, and further wherein the compound has a structural Formula represented by Formula II, or Formula III, wherein Formula II is Formula II

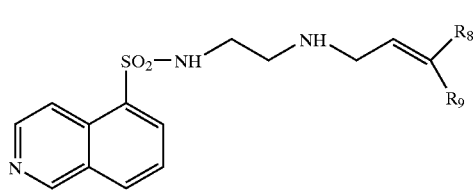

wherein $R_8$ and $R_9$ are independently selected from the group consisting of substituted or unsubstituted phenyl, alkylaryl, naphthyl, quinolyl, or a halogen, wherein at least one of $R_8$ and $R_9$ is aromatic, and Formula III is

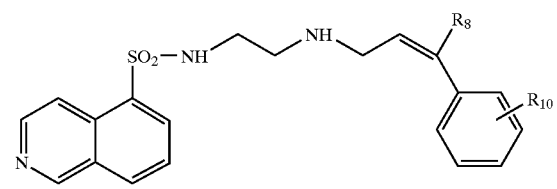

wherein $R_8$ is selected from the group consisting of substituted or unsubstituted phenyl, alkylaryl, naphthyl, quinolyl, or a halogen; and $R_{10}$ is selected from the group consisting of hydrogen, a lower alkyl group, a lower alkoxy group, substituted or unsubstituted phenyl group, a lower alkyl substituted with at least one substituent selected from the group consisting of phenyl group, a halogen, hydroxyl, thiol, nitro, cyano, or amino group.

19. The method of claim 17, wherein the compound is a compound of general formula V, and further wherein the compound has structural Formula VI

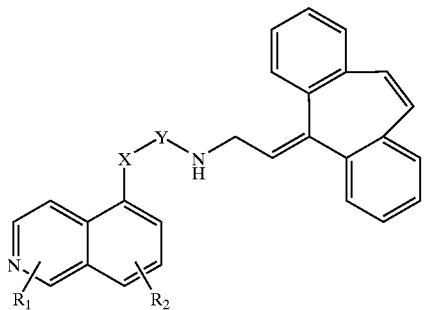

Formula VI wherein X is selected from the group consisting of $SO_2$—NH, S and O;

Y represents substituted or unsubstituted alkylene of 1–4 carbons atoms;

$R_1$ and $R_2$ are independently selected from the group consisting of hydrogen, a lower alkyl group, a lower alkoxy group, substituted or unsubstituted phenyl group, a lower alkyl substituted with at least one substituent selected from the group consisting of phenyl group, a halogen, hydroxyl, thiol, nitro, cyano, or amino group.

20. The method of claim 17, wherein the compound is administered as the active ingredient of a pharmaceutical composition that includes a carrier or diluent.

21. The method of claim 17, wherein the inhibition of a protein kinase assists in the treatment of ovarian cancer, glioma and pancreatic cancer.

* * * * *

UNITED STATES PATENT AND TRADEMARK OFFICE
CERTIFICATE OF CORRECTION

PATENT NO. : 6,949,565 B2
DATED : September 27, 2005
INVENTOR(S) : Livnah et al.

It is certified that error appears in the above-identified patent and that said Letters Patent is hereby corrected as shown below:

Title page,
Item [56], References Cited, FOREIGN PATENT DOCUMENTS, after "JP 02256666", change "12/1989" to -- 10/1990 --.
OTHER PUBLICATIONS, "Shinya Wakusawa et al." reference, after "Molecular Pharmacology," insert -- (1992) --; and
"K.-I. Miyamoto et al." reference, after "Cancer letters," insert -- (1990) --.

Column 28,
Lines 26 and 35, after "substituted with at", change "lest" to -- least --.
Line 44, after "quinolyl or a", change "hydrogen" to -- halogen --.
Line 61, after "alkylaryl," change "naplithyl" to -- naphthyl --.

Column 29,
Lines 50 and 57, after "substituted with at", change "lest" to -- least --.
Line 54, after "carbonyl," change "carbaniate" to -- carbamate --.

Signed and Sealed this

Twenty-ninth Day of November, 2005

JON W. DUDAS
*Director of the United States Patent and Trademark Office*

SEQUENCE LISTING

<160> NUMBER OF SEQ ID NOS: 3

<210> SEQ ID NO 1
<211> LENGTH: 7
<212> TYPE: PRT
<213> ORGANISM: artificial sequence
<220> FEATURE:
<223> OTHER INFORMATION: substrate peptide

<400> SEQUENCE: 1

Arg Pro Arg Thr Ser Ser Phe
1               5

<210> SEQ ID NO 2
<211> LENGTH: 6
<212> TYPE: PRT
<213> ORGANISM: artificial sequence
<220> FEATURE:
<223> OTHER INFORMATION: substrate peptide
<220> FEATURE:
<221> NAME/KEY: MISC_FEATURE
<222> LOCATION: (2)..(2)
<223> OTHER INFORMATION: unknown or other
<220> FEATURE:
<221> NAME/KEY: MISC_FEATURE
<222> LOCATION: (4)..(4)
<223> OTHER INFORMATION: unknown or other
<220> FEATURE:
<221> NAME/KEY: MISC_FEATURE
<222> LOCATION: (5)..(5)
<223> OTHER INFORMATION: unknown or other
<220> FEATURE:
<221> NAME/KEY: MISC_FEATURE
<222> LOCATION: (6)..(6)
<223> OTHER INFORMATION: Ser or Thr

<400> SEQUENCE: 2

Arg Xaa Arg Xaa Xaa Xaa
1               5

<210> SEQ ID NO 3
<211> LENGTH: 12
<212> TYPE: PRT
<213> ORGANISM: artificial sequence
<220> FEATURE:
<223> OTHER INFORMATION: substrate peptide

<400> SEQUENCE: 3

Lys Gly Arg Pro Arg Thr Ser Ser Phe Ala Glu Gly
1               5                   10